United States Patent [19]
Chelveder

[11] Patent Number: 5,726,745
[45] Date of Patent: Mar. 10, 1998

[54] PROCESS AND APPARATUS FOR PREPARING A BLOOD SAMPLE FOR ANALYSIS OF WHITE BLOOD CELLS

[75] Inventor: Jean-Claude Chelveder, Vitteaux, France

[73] Assignee: Hycel Groupe Lisabio, Morangis, France

[21] Appl. No.: 686,760

[22] Filed: Jul. 26, 1996

[51] Int. Cl.⁶ .......................... G01N 33/48; G01N 21/00; G01N 21/55

[52] U.S. Cl. .............. 356/39; 356/433; 356/448; 436/17; 436/172; 436/166

[58] Field of Search .................. 356/39, 40, 335, 356/336, 415, 427, 184, 197, 433; 250/214 D, 214 C, 214 L, 573; 436/17, 63, 172, 800, 166, 174

[56] References Cited

U.S. PATENT DOCUMENTS

| | | | |
|---|---|---|---|
| 3,622,795 | 11/1971 | Dorman, Jr. et al. | 250/218 |
| 4,125,327 | 11/1978 | Margolis | 356/39 |
| 4,876,069 | 10/1989 | Jochimsen | 422/73 |
| 5,045,474 | 9/1991 | Becker | 436/63 |
| 5,071,247 | 12/1991 | Markosian et al. | 356/39 |
| 5,138,181 | 8/1992 | Lefevre et al. | 250/573 |
| 5,182,617 | 1/1993 | Yoneyama et al. | 356/440 |
| 5,264,369 | 11/1993 | Sakata et al. | 436/63 |
| 5,416,026 | 5/1995 | Davis | 436/66 |
| 5,427,920 | 6/1995 | Berndt et al. | 435/34 |
| 5,449,622 | 9/1995 | Yabe et al. | 436/63 |
| 5,471,294 | 11/1995 | Ogino | 356/73 |
| 5,510,267 | 4/1996 | Marshall | 436/63 |

FOREIGN PATENT DOCUMENTS

| | | | |
|---|---|---|---|
| 0627624 | 12/1994 | European Pat. Off. | G01N 33/50 |
| 2384260 | 10/1978 | France | G01N 33/16 |

OTHER PUBLICATIONS

Database WPI, Week 9227, Derwent Publications Ltd., London, GB; AN 92-22382 & JP-A-04 151 541 (Hitachi Keisoku Eng KK), May 25, 1992; Abstract.

Patent Abstracts of Japan, vol. 013 No. 162 (P-859), Apr. 19, 1989 & JP-A-64 000450 (Terumo Corp) Jan. 5, 1989; Abstract.

Primary Examiner—Frank G. Font
Assistant Examiner—Michael P. Stafira
Attorney, Agent, or Firm—Jacobson, Price, Holman & Stern, PLLC

[57] ABSTRACT

A process and apparatus for preparing blood for analysis of white blood cells involves:

preparing a mixture made up of blood and a lysing agent, emitting luminous radiation in the direction of the mixture, receiving the light emitted through the mixture, comparing the quantity of light received at a pre-determined threshold, the process of erythrolysis, being complete when the quantity of light corresponds to the threshold and, neutralizing the action of the lysing agent when erythrolysis is completed by the addition of an appropriate reagent.

7 Claims, 2 Drawing Sheets

PROCESS AND APPARATUS FOR PREPARING A BLOOD SAMPLE FOR ANALYSIS OF WHITE BLOOD CELLS

FIELD OF THE INVENTION

The invention relates to the field of cytology with particular reference to analyses practiced in hematology.

It relates to a process and apparatus for preparing blood with a view to white blood cell analysis, consisting in re-establishing as quickly as possible the physiological conditions respecting the integrity of the leucocytes following the destruction of the erythrocytes (i.e. red blood cells) by a lysing agent.

BACKGROUND OF THE INVENTION

The hematological analyses aim at providing an identification and count of several cell categories in order to establish a diagnosis. The cells to be recognized are usually red blood cells, platelets and white blood cells, the last of these three being divided into several families such as lymphocytes, monocytes and various granulocytes.

They are usually carried out by means of an apparatus using the Coulter effect. This consists of passing cells in a conductive liquid through an aperture of narrow diameter, to which a constant direct current is applied. The passage of a particle causes a transitory variation of conductivity, representative of the volume taken up by the passing particle.

However, it is recognized that these measurements of impedance variations are insufficient for identifying the different families of leucocytes, since cells belonging to different families sometimes have very similar volumes.

It is for this reason that these impedance variation measurements are traditionally accompanied by measurements using an optical apparatus, for example a laser. In such an apparatus, the cells centered and isolated from each other by hydrodynamic focusing, are illuminated by a laser beam and reflect light. The light reflected at a wide angle (90°) has an intensity in correlation with the internal structure of each cell.

It is observed that, using information concerning the volume and internal structure of the cells, it is possible to obtain useful information with a view to the classification of the different families of white blood cells.

Irrespective of the apparatus used for hematological analyses, it is necessary to prepare beforehand samples of the blood to be analysed.

Since red blood cells are 500 to 1000 times more numerous than white blood cells, they must be removed from the sample so that the analytical apparatus can count and identify the white blood cells.

In standard practice, a lysing agent is added to the blood sample in order to destroy the red blood cells.

This reagent also acts on the white blood cells although they are more resistant than the red blood cells. In order to prevent the destruction of the white blood cells, the lysing action must be stopped once the red blood cells are destroyed.

To this end, a quenching reagent which halts lysing is added to the sample.

The techniques used up to now are based on a chemical control of the lysing process. Thus, for all samples, temperature and all other relevant parameters are kept constant and the quenching reagent is injected at a determined time which does not vary from one sample to another.

On the whole, these techniques prove satisfactory. However, in a certain number of cases, the samples are not properly prepared and cannot undergo valid analysis. These samples either contain too many red blood cells, in which case the erythrolysis reaction (or lysing reaction of the red blood cells) has been stopped too soon, or a small number of red cells, in which case the lysing agent has attacked the white blood cells which may be partially destroyed by the lysing action which has continued for too long.

In the former case, the analytical apparatus cannot detect the white blood cells because of the presence of the red blood cells.

In the latter case, the analysis results cannot be taken into consideration. In fact, as pointed out earlier, traditional analysis apparatus make use of impedance measurements to determine the number and volume of the cells, and light diffusion measurements to determine their internal structure. These measurements are therefore not valid unless the white blood cells are unharmed and unless, in particular, their membranes are intact. If the white blood cells are destroyed to such an extent that their size is below the count threshold, the count result of the white blood cells is inaccurate by default. Even if there is limited destruction of the cells and the count is correct, their volume is still reduced to a greater or lesser degree and the change of state of their cytoplasmic membrane and of their cellular content has a very considerable effect on the amount of light diffused and consequently on the differential capability of the leucocyte subpopulations.

These flawed analyses have important repercussions for a laboratory. First of all, they may be a cause of error in diagnosis with all that it implies for the patient. Secondly, when the laboratory has succeeded in detecting the abnormalities in the analysis results, it has to carry out a new analysis, possibly using less sophisticated techniques.

As a result, the proportion of imperfect analyses is extremely detrimental, both in terms of medical risk and additional costs for laboratories.

Essentially, the invention aims at remedying these drawbacks by providing a process and apparatus which make it possible to re-establish as quickly as possible the conditions respecting the integrity of the leucocytes at the end of the destruction process of the red blood cells (erythrolysis).

BRIEF SUMMARY OF THE INVENTION

The invention relates to a process consisting of:
preparing a mixture made up of blood and a lysing agent,
emitting luminous radiation in the direction of said mixture,
receiving the light emitted through said mixture,
comparing the quantity of light received at a predetermined threshold, erythrolysis being complete when the quantity of light corresponds to said threshold, and
distributing a reagent neutralizing the effect of the lysing agent, re-establishing the conditions favourable to maintaining the physiological state of the leucocytes.

This process makes it possible to determine the moment when the erythrolysis process is complete for any type of blood and thus to take into account the differences which may exist from one blood type to another.

The invention also relates to an apparatus for preparing a blood for analysis, comprising:
an optical apparatus emitting luminous radiation in the direction of a mixture constituted of blood and a lysing agent, means for receiving the light emitted through said mixture, characterized in that said apparatus also comprises:

comparator means, of which a first input corresponds to a pre-determined threshold value, a second input receiving a signal representative of the light received by said means of reception, the output value of said comparator means being approximately equal to 0 when the erythrolysis process is complete, and means for injecting a lysing neutralization agent.

The following characteristics of the apparatus may also be considered, separately or according to all their possible technical combinations:

the optical apparatus comprises an electro-luminescent diode whose luminous radiation is focused by appropriate means, the means for receiving the light emitted through the mixture are constituted by a photodiode, the photodiode is connected to means delivering a voltage signal representative of the light received by the photodiode, the apparatus includes a tank for the mixture, the apparatus includes means for homogenizing the mixture in the tank.

BRIEF DESCRIPTION OF THE DRAWINGS

A clearer picture of the invention, together with other aims, advantages and characteristics will emerge from the ensuing description of non limitative examples of embodiments, which description is to be read in conjunction with the accompanying drawings in which.

DETAILED DESCRIPTION OF THE INVENTION

Figure 1:
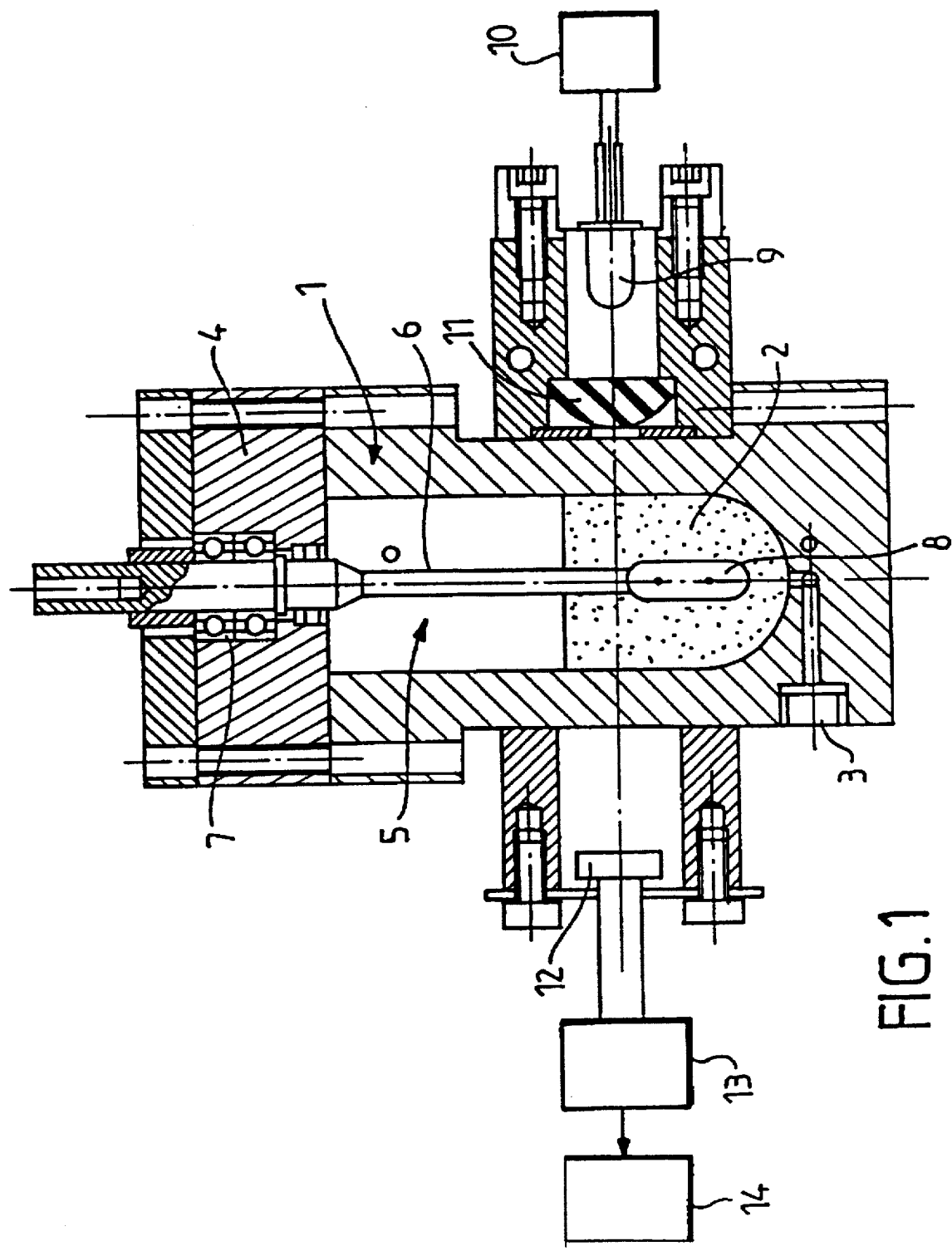
FIG. 1 represents schematically an apparatus according to the invention.

With reference to FIG. 1, the apparatus according to the invention comprises a tank 1 designed to contain a mixture 2, made up of a blood sample and a determined quantity of lysing agent. These products are introduced by the channel 3 and come from means not represented in FIG. 1.

The tank is closed by a lid 4.

The apparatus comprises means 5 for stirring the mixture and thus ensuring good homogeneity. These means consists of a rod 6 extending into the tank 1 and fixed in rotation in the lid 4 by means of a bearing 7.

A system ensuring the rotation of the rod 6 in the tank is provided and is not represented in the Figure.

At its extremity, the rod 6 includes a part 8 in the form of a blade.

The detection apparatus according to the invention also comprises means 9 of emitting luminous radiation. These means may, for example, consist of an electro-luminescent diode. This diode is supplied with electric current by standard means 10.

The means 9 of luminous radiation emission are arranged in such a way that the radiation crosses the tank.

The apparatus also contains focusing means 11, such as a focusing lens which is centered on the principal emission axis of the luminous radiation.

Thus, the diode 9 emits luminous radiation in the direction of the lens 11. This radiation constitutes a beam of light directed towards the tank 1 and the mixture 2 which it contains.

The apparatus also comprises means 12 for receiving the light after it has passed through the tank 1; these means of reception may notably consist of a photodiode.

The means of light reception 12 are connected to a system 13 which delivers a signal representative of the quantity of light received by the means 12.

Figure 2:
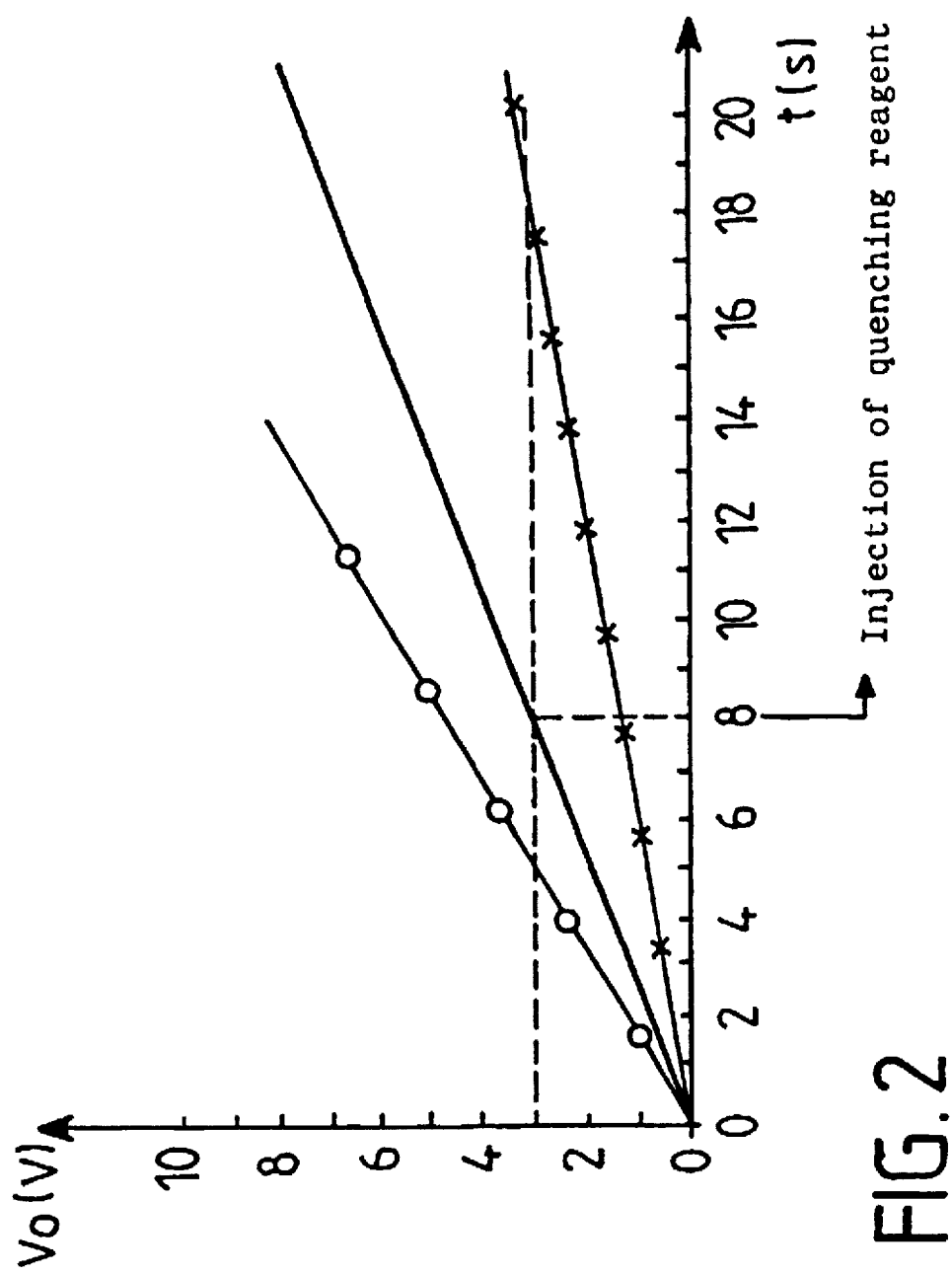
FIG. 2 illustrates, in function of time, three examples of the output voltage evolution of the photodiode amplifier illustrated in FIG. 1.

In the case of a photodiode, said photodiode may be connected to an amplifier, delivering an output voltage V0. FIG. 2 illustrates the output voltages obtained, for this embodiment. Depending on its composition, the mixture absorbs to a greater or lesser degree the light emitted by the electro-luminescent diode, and the light received by the photodiode 12 and the output voltage V0 of the amplifier 13 also vary in amounts.

The apparatus works as follows. When the mixture 2 is introduced in the tank 1, the lysing agent has not yet affected the blood cells. This mixture generally comprises about 30 μl to which a lysing agent has been added.

The mixture, which is very cloudy, absorbs the luminous radiation emitted by the electro-luminescent diode 9 almost entirely. The voltage from the amplifier 13 is thus approaching 0, as indicated in FIG. 2.

In the course of time, the lysing agent produces its effect and the red blood cells are destroyed. The quantity of light received by the photodiode then increases, along with the output voltage V0 of the amplifier 13.

This is illustrated by FIG. 2 which shows three examples of output voltage V0 evolution.

In FIG. 2 and as an example, the threshold value of 3 volts is considered as representative of a mixture in which the red blood cells are destroyed, the white blood cells still being intact. This threshold therefore corresponds to the end of the erythrolysis process and to the moment when the lyse must be quenched.

The unbroken straight line corresponds to an average lysing time, the threshold value of 3 volts being reached after about 8 seconds. The straight line consisting of alternating dashes and circles (-o-o-) corresponds to a shorter lysing time, about 5 seconds, and the straight line consisting of alternating dashes and crosses (-x-x-) to a longer lysing time, of about 19 seconds.

The apparatus according to the invention includes means for detecting that the threshold value is reached. They may notably consist of a comparator 14 of which a first input is fixed on the previously determined threshold value, a second input receiving the signal emitted by the means 13, representative of the light received by the reception means 12. When the output of the comparator is approximately equal to 0, the mixture present in the tank 1 is ready to undergo analysis, the red blood cells having been destroyed and the white blood cells still being intact. As soon as this value has been detected, the action of the lysing agent must be neutralized. This is notably obtained here by dilution with a saline solution at 9 grams per liter of NaCl.

The examples illustrated in FIG. 2 show that the apparatus and process according to the invention make it possible to adapt to the differences existing from one blood sample to another.

The sample corresponding to a mean erythrolysis time of 8 seconds could in fact have been obtained in a valid way according to standard techniques, but this is not the case for the two other examples whose lysing times are respectively 5 and 19 seconds. In point of fact, these standard techniques are based on a fixed lysing time and a mean value, notably 8 seconds. Thus, blood whose lysing time is 5 seconds would also include destroyed white blood cells if it were prepared according to a standard technique which would continue lysing for 3 extra seconds. Similarly, a blood sample whose lysing time is 19 seconds would include red blood cells if it were prepared according to standard techniques, since lysing would be halted after 8 seconds.

The numerous tests carried out using the process and the apparatus according to the invention have revealed no case in which the blood is incompletely lysed (leaving red blood cells intact) or over-lysed (having destroyed white blood cells).

Thus, the process and the apparatus according to the invention make it possible to overcome the drawbacks of known techniques by no longer using a fixed lysing time but by adapting it to each type of blood prepared. In this way, said process and apparatus make it possible to take into account the differences existing from one blood sample to another, these differences depending notably on the age of the sample, that is to say on the moment when it was collected from the patient. So-called autolysis phenomena have in fact been observed when the sample has been stored for too long.

It will be apparent to one skilled in the art that several variations may be made without departure from the spirit and scope of the claimed invention.

I claim:

1. A process for preparing blood for analysis of white blood cells and comprising:

preparing a mixture made up of blood and a lysing agent, emitting luminous radiation in the direction of the mixture, receiving the light emitted through said mixture, characterized in that the process then consists of:

comparing the quantity of light received at a pre-determined threshold, erythrolysis being complete when the quantity of light corresponds to said threshold, and neutralizing the action of the lysing agent, when erythrolysis is completed.

2. Apparatus for preparing blood for analysis of white blood cells comprising:

an optical apparatus emitting luminous radiation in the direction of a mixture of said blood and a lysing agent, means for receiving the light emitted through said mixture, characterized in that the apparatus also comprises:

comparator means of which a first input is set at a pre-determined threshold value, a second input receiving a signal representative of the light received by said means of reception, the output value of said comparator means being approximately equal to 0 when the process of erythrolysis is complete and means for injecting an agent for neutralizing the lyse.

3. Apparatus according to claim 2, in which the optical apparatus comprises an electro-luminescent diode whose luminous radiation is focused by means.

4. Apparatus according to claim 2, in which the means of receiving the light emitted through the mixture are constituted by a photodiode.

5. Apparatus according to claim 4, in which the photodiode is connected to means delivering a voltage signal representative of the light received by the photodiode.

6. Apparatus according to claim 2, comprising a tank designed to contain said mixture.

7. Apparatus according to claim 6, comprising means for homogenizing the mixture in said tank.

* * * * *